(12) United States Patent
Laville et al.

(10) Patent No.: US 9,750,762 B2
(45) Date of Patent: Sep. 5, 2017

(54) USE OF YEAST FLAKES FOR TREATING AND/OR PREVENTING HYPERINSULINEMIA

(75) Inventors: Martine Laville, Charly (FR); Julie-Anne Nazare, Lyons (FR); Eric Oriol, Champigny sur Marne (FR)

(73) Assignee: Lesaffre et Compagnie, Paris (FR)

( * ) Notice: Subject to any disclaimer, the term of this patent is extended or adjusted under 35 U.S.C. 154(b) by 505 days.

(21) Appl. No.: 12/670,436

(22) PCT Filed: Jul. 25, 2008

(86) PCT No.: PCT/EP2008/059815
§ 371 (c)(1),
(2), (4) Date: Jan. 25, 2010

(87) PCT Pub. No.: WO2009/013357
PCT Pub. Date: Jan. 29, 2009

(65) Prior Publication Data
US 2010/0196413 A1 Aug. 5, 2010

(30) Foreign Application Priority Data
Jul. 25, 2007 (FR) .................................... 07 56731

(51) Int. Cl.
*A61K 31/716* (2006.01)
*A61K 31/736* (2006.01)
*A61K 36/064* (2006.01)

(52) U.S. Cl.
CPC .......... *A61K 31/716* (2013.01); *A61K 31/736* (2013.01); *A61K 36/064* (2013.01)

(58) Field of Classification Search
None
See application file for complete search history.

(56) References Cited

U.S. PATENT DOCUMENTS

| 2004/0151738 A1 | 8/2004 | Oriol et al. |
| 2006/0257422 A1 | 11/2006 | Lesaffre |

FOREIGN PATENT DOCUMENTS

| EP | 1 094 117 A1 | 4/2001 |
| FR | 2 825 004 A1 | 11/2002 |
| JP | 61-167622 A | 7/1986 |
| WO | WO 2005/021015 A1 | 3/2005 |

OTHER PUBLICATIONS

Biorklund M et al., "Changes in serum lipids and postprandial glucose and insulin concentrations after consumption of beverages with {beta}-glucans from oats or barley: A randomised dose-controlled trial", European Journal of Clinical Nutrition, Nov. 2006, pp. 1272-1281, vol. 59, No. 11, Elsevier Science Publishers, Amsterdam, XP002476553.
Canterbury & Nelson Nutraceuticals: New Zealand/Gracelinc Ltd., "Glucagel", Online, 2002, pp. 1-2, XP002476551.
Canterbury & Nelson Nutraceuticals: New Zealand/Gracelinc Ltd., Glucagel, "Barley beta-glucan and healthy blood glucose", Online, pp. 1-3, XP002476552.
Database WPI WEEK198636, "Diabetes Controlling Drug—Comprises Cell Wall of Beer Yeast Contg. Edible Fibre", Thomson Scientific, London, GB, XP002476554, Abstract of B4 : Jul. 29, 1986.
Kim Yea-Woon, et al., "Anit-diabetic activity of beta-glucans and their enzymatically hydrolyzed oligosaccharides from Agaricus blazei", Biotechnology Letters, Apr. 2005, pp. 483-487, vol. 27, No. 7, XP002476549.
Jenkins Al et al., "Depression of the glycemic index by high levels of beta-glucan fiber in two functional foods tested in type 2 diabetes", European Journal of Clinical Nutrition, 2002, pp. 622-628, vol. 56, No. 7, XP002476550.
International Search Report dated Nov. 25, 2008 including English translation Eight (8) pages).
Lustig, Robert, Childhood obesity: behavorial aberration or biochemical drive? Reinterpreting the First Law of Thermodynamics, Nature Clinical Practice Endocrinology & Metabolism, Aug. 2006, vol. 2, No. 2, pp. 447-458.
Shanik, Michael et al., Insulin Resistance and Hyperinsulinemia is hyperinsulinemia the cart or the horse?, Diabetes Care, vol. 31, Supplement 2, Feb. 2008, p. 5262-5268.
Mauvais-Jarvis, F. et al., Therapeutic Perspectives for Type 2 Diabetes Mellitus: Molecular and Clinical Insights, Diabetes Metab (Paris), 2001, 27, pp. 415-423.
Steven Kahn et al., "Mechanisms Linking Obesity to Insulin Resistance and Type 2 Diabetes", Insight Review, Dec. 14, 2006, pp. 840-846, vol. 444, Nature Publishing Group.
Mohammed Qatanani et al., "Mechanisms of Obesity-Associated Insulin Resistance: Many Choices on the Menu", genesdev.cship.org, 2007, pp. 1443-1455, Cold Spring Harbor Laboratory Press ISSN 0890-9369/07; www.genesdev.org.
Scott M. Grundy, MD, Ph.D., "Hypertriglyceridemia, Insulin Resistance, and the Metabolic Syndrome", The American Journal of Cardiology, May 13, 1999, pp. 25F-29F, vol. 83 (9B), Excerpta Medica, Inc.

*Primary Examiner* — Amy L Clark
(74) *Attorney, Agent, or Firm* — Crowell & Moring LLP

(57) ABSTRACT

The invention relates to the use of yeast flakes for preparing a pharmaceutical composition for treating and/or preventing hyperinsulinemia.

21 Claims, 2 Drawing Sheets

USE OF YEAST FLAKES FOR TREATING AND/OR PREVENTING HYPERINSULINEMIA

The present invention concerns the use of yeast cell walls for the treatment and/or prevention of hyperinsulinaemia.

Insulin is a hypoglycaemic hormone secreted by the β cells of the pancreatic islets of Langerhans. Insulin can reduce glycaemia, in particular by activating transport of glucose into target tissues (muscle, liver and adipose tissues).

Type-2 diabetes is characterized by insulin-resistance translating, during a first phase, as hyperinsulinism. Some obesities are also associated with hyperinsulinism. For diabetes with insulin-resistance, medicinal products which can reduce excess blood sugar without stimulating the secretion of insulin can be prescribed (for example Metformin).

Document JP-A-61-167622 proposes an agent to combat diabetes containing a cell fraction of beer yeast, called cell wall in this document, and obtained by hydrolysis of debittered beer yeast for at least 2 hours at a temperature of 50 to 70° C. and aqueous extraction of the water-soluble constituents. Said cell fraction of beer yeast notably has a glucan content of around 14.8%, a mannan content of around 13.9%. Said cell fraction also has a glycogen content of around 24.9%. Glycogen is a reserve polysaccharide also present in the muscles and in particular in the liver. This glycogen is also a reserve substance of yeast, used by yeast as an energy source to ensure its survival. While it is one of the main constituents of the cell fraction in this Japanese application, it does not form part of the cell wall of yeasts.

Patent application WO2005/021015 describes the use of yeast cell walls for the prevention and treatment of hyperglycaemia and stabilization of glycaemia, said yeast cell walls having a low glycogen content and able to be obtained using a simple enzymatic autolysis or hydrolysis method. The total glucan and mannan content of said yeast cell walls is at least 34.0% by weight of dry matter.

The β-glucans of the cell wall of yeast are essentially glucose polymers whose glucose units in the main chain are linked by β-1,3 bonds and whose branches are linked by β-1,6 bonds. The β-glucans of yeast are insoluble and have low viscosity.

The β-glucans purified from the yeast cell wall have immunostimulating properties. In particular, it has been shown that the β-glucans of yeast are capable of binding to macrophages and of activating them. The β-glucans of yeast are studied for antibacterial, antiviral and antitumoral applications (Adams D. S., Journal of Leukocyte Biology, 1997).

The subject-matter of the present invention is the use of yeast cell walls as insulin-regulating agent.

One subject of the invention is notably the use of yeast cell walls for the treatment and/or prevention of hyperinsulinaemia.

One subject of the present invention is the use of yeast cell walls for the preparation of a pharmaceutical composition intended for the treatment and/or prevention of hyperinsulinaemia, said yeast cell walls having:
  a total glucan and mannan content of at least 34.0% dry matter content by weight, and
  a glycogen content of less than 10.0% dry matter content by weight.

The term <<yeast cell walls>> refers to the insoluble fraction of the yeast cells, non-chromium enriched, obtained after autolysis or enzymatic hydrolysis, essentially, by proteases, leading to solubilisation of at least 50% and preferably at least 60% by weight of dry matter of the whole yeast cells and preserving the structural polysaccharides of the cell wall i.e. the β-glucans and mannans, these mannans being in the form of mannoproteins.

This autolysis or enzymatic hydrolysis is conducted so as to solubilise most of the reserve sugars of the yeast cell i.e. glycogen and trehalose. The yeast cell walls are obtained by separating the solubilised fraction using autolysis or enzymatic hydrolysis, preferably for a time of at least 18 hours. Preferred yeast cream autolysis methods are described pages 370 to 377 in the reference work <<Yeast Technology>> $2^{nd}$ edition, 1991, G. Reed and T. W. Nogodawithana, published by Van Nostrand Reinhold, New York, ISBN 0-442-31892-8. The yeast cell walls thus obtained are then typically dried using a conventional drying method such as spray drying or drying on heated rolls.

The yeast cell walls of the invention have a total glucan and mannan content in the cell wall (systematically expressed in equivalent weight of glucose and mannose respectively—see measurement methods below) of at least 34.0% by weight of dry matter and a glycogen content (systematically expressed in glucose equivalent weight—see measurement methods below) of less than 10.0% by weight of dry matter.

By <<hyperinsulinaemia>> is meant both basal hyperinsulinaemia and postprandial hyperinsulinaemia. In one advantageous embodiment, the yeast cell walls of the invention are used for the prevention and/or treatment of postprandial hyperinsulinaemia. Alternatively, the yeast cell walls of the invention are used for the prevention and/or treatment of basal hyperinsulinaemia. In another embodiment, the yeast cell walls of the invention are used for the prevention and/or treatment of both basal hyperinsulinaemia and postprandial hyperinsulinaemia.

Basal hyperinsulinaemia is characterized by a high basal plasma insulin level. The basal level corresponds to insulin levels between meals, notably when the person is fasting. The physiological basal level is generally equal to, or lower than 10 mU/L in a slim, healthy individual. Therefore basal hyperinsulinaemia can be characterized by a basal level between meals (notably when fasting) of more than 10 mU/L.

Postprandial hyperinsulinaemia corresponds to an excessive insulin response after food intake.

Postprandial hyperinsulinaemia can be evidenced by an oral glucose tolerance test (OGTT). The physiological response to the OGTT test is characterized by an insulin secretion peak of generally between 30 and 60 mU/L in a healthy slim individual. Therefore postprandial hyperinsulinaemia can be characterized by an OGTT response with an insulin secretion peak of more than 60 mU/L.

A patient's plasma insulin level is measured using conventional techniques known to persons skilled in the art. In particular an RIA test (RadioImmuno-Assay) can be performed on a plasma sample taken from a patient (for example RIA, Biosurce, Medgenix Diagnostics, Rungis, France).

The objective of hyperinsulinaemia treatment is to reduce the basal plasma insulin level and/or to restore a physiological insulin response after food intake.

The objective of hyperinsulinaemia prevention is notably to maintain the basal plasma insulin level at physiological values and/or to maintain a physiological insulin response after food intake.

The subject-matter of the invention is particularly the treatment and/or prevention of postprandial hyperinsulinaemia.

The subject of the invention is particularly the use such as defined above, wherein the yeast cell walls are of the genus *Saccharomyces cerevisiae*.

Said yeasts are preferably bakers' yeasts. A baker's yeast is a yeast belonging to the species *Saccharomyces cerevisiae*, produced essentially by aerobic proliferation or culture as taught in the reference work <<Yeast Technology>> cited above, and which has not been used for any purpose before its autolysis or enzymatic hydrolysis, contrary to beer yeast for example which is a sub-product from the manufacture of beer and has therefore served to manufacture beer before being collected for enzymatic autolysis or hydrolysis. This beer yeast was essentially cultured under anaerobia (the production of beer being an anaerobic process).

The subject of the present invention is the use such as defined above, wherein said yeast cell walls have a total glucan and mannan content of at least 40.0% dry matter content by weight, preferably at least 45.0% dry matter content by weight.

The yeast cell walls of the invention usefully have a protein content N×6.25 of 17.0 to 35.0% dry matter content by weight, preferably 18.0 to 26.0% dry matter content by weight.

A particular subject of the invention is the use such as defined above wherein said yeast cell walls have a mannan content of less than 30% dry matter content by weight.

In one preferred embodiment of the invention, the mannan content of the yeast cell walls lies between 20 and 26% dry matter content by weight. This embodiment corresponds to yeast cell walls obtained by enzymatic autolysis or hydrolysis, separation of the solubilised fraction and drying of the non-soluble fraction such as described previously and in Example 1.1 (section headed: *Preparation of yeast cell walls containing mannans*). Said product, after an oral glucose tolerance test (OGTT), allows a reduced insulin peak to be obtained compared with a placebo in patients suffering from type-2 diabetes (see Example 2).

The subject of the invention is notably the use such as defined above, wherein said yeast cell walls have a mannan content of less than 2% dry matter content by weight, notably less than 1% dry matter content by weight, notably less than 0.1% dry matter content by weight.

In another preferred embodiment of the invention, the mannan content of the yeast cell walls is lower than 0.1% dry matter content by weight.

The mannans can be removed by hot alkaline treatment. Hot alkaline treatment consists of placing in an aqueous suspension the yeast cell walls of the invention obtained as described above, and of heating the suspension in an alkaline medium at between 70° C. and 100° C. for a maximum time of three hours. The fraction solubilised by this treatment containing most of, even all, the mannoproteins is removed by centrifuging and washing. The remaining non-solubilised fraction is collected and generally dried.

Preferably the mannans are removed by hot alkaline treatment followed by an acid treatment for full removal the mannans.

These treatments are detailed in the Examples section.

With said products obtained from the preceding yeast cell walls, subjected to hot alkaline treatment and optionally to acid treatment such as described previously (see also Example 1.1 section headed: *Preparation of yeast cell walls devoid of mannans*) and in which the mannans have been fully or almost fully removed (the glucans representing most of the total content of glucans and mannans), it is possible after an OGTT test to obtain a reduced insulin peak compared with a placebo, and even compared with yeast cell walls in which the mannans have not been removed, in patients suffering from type-2 diabetes or from overweight (see Example 2).

The subject of the present invention is the use such as defined above, wherein the yeast cell walls have a total glucan and mannan content equal to or less than 90% dry matter content by weight, notably equal to or less than 80% dry matter content by weight, notably equal to or less than 70% dry matter content by weight.

The subject of the present invention is more particularly the use such as defined above, wherein the yeast cell walls have a total glucan and mannan content of 45 to 90% dry matter content by weight, notably 52% to 80% dry matter content by weight, preferably 65% to 77% dry matter content by weight, and further preferably 72% to 77% dry matter content by weight. Therefore according to one particularly advantageous embodiment the glucan and mannan content lies between 72% to 77% dry matter content by weight.

Notably, in one particular embodiment, the subject of the present invention is the use such as defined above, wherein the glucan and mannan content lies between 72% and 77% dry matter content by weight, and the mannan content is less than 2% dry matter content by weight notably less than 1% dry matter content by weight, notably less than 0.1%.

Alternatively, the glucan and mannan content may also be equal to or less than 55% dry matter content by weight, provided that it remains higher than 45% dry matter content by weight.

Therefore according to one advantageous embodiment, the glucan and mannan content lies between 52% and 57% dry matter content by weight.

Notably in one particular embodiment, the subject of the present invention is the use such as defined above, wherein the glucan and mannan content lies between 52% to 57% dry matter content by weight, and the mannan content is less than 2% dry matter content by weight, notably less than 1% dry matter content by weight, notably less than 0.1%.

The subject of the present invention is the use such as defined above, wherein the yeast cell walls have a glycogen content of less than 8.0% dry matter content by weight, preferably less than 5.0% dry matter content by weight, preferably less than 3.0% dry matter content by weight, preferably less than 1.0% dry matter content by weight, and further preferably less than 0.1% dry matter content by weight.

To remove the glycogen fully or almost fully from the yeast cell walls, the yeast cell walls of the invention can be subjected to a hot alkaline treatment such as described above, and preferably a hot alkaline treatment followed by an acid treatment.

With said treatment it is possible to produce yeast cell walls according to the invention having a total glucan and mannan content of 45% to 90% dry matter content by weight, preferably 52% to 80% dry matter content by weight, preferably 65% to 77% dry matter content by weight, and further preferably 72 to 77% dry matter content by weight. With said treatment it is possible in particular to produce yeast cell walls which also contain less than 1.0% dry matter content by weight of glycogen, preferably less than 0.1% dry matter content by weight of glycogen.

The pharmaceutical composition according to the invention can be administered in different forms or presentations.

The pharmaceutical composition according to the invention comprises at least one active substance represented by the yeast cell walls and a pharmaceutically acceptable vehicle.

The pharmaceutical composition of the invention may comprise one or more other active substances, for example chosen from among hypoglycaemic or insulin-sensitizing agents, and notably from among hypoglycaemic sulfamides, biguanide, metformin and thiazolidinedione derivatives, inhibitors of α-glucosidases.

The preparation can also contain one or more vitamins, notably chosen from among vitamin A, vitamin C, vitamin D, vitamin E, vitamin K, vitamins B1 (thiamine), B2 (riboflavin), B3 (niacin), B5 (pantothenic acid), B6, B8 (biotin), B9 (folic acid), B12 (cobolamine) and/or one or more food minerals notably chosen from among calcium, phosphorus, potassium, sodium, magnesium and iron.

The subject of the present invention is also pharmaceutical compositions such as defined above containing chromium.

The pharmaceutical composition may contain one or more pharmaceutically acceptable excipients.

In one preferred embodiment, the pharmaceutical composition according to the invention is suitable for administration via oral route.

The pharmaceutical composition can notably be in the form of a tablet, capsule, pill, powder, granule or suspension.

The pharmaceutical composition of the invention can in particular be in the form of a dose intake corresponding to a quantity of dry matter of yeast cell walls according to the invention of less than 10 g, preferably 8 to 9 g.

In one preferred embodiment, the subject of the present invention is the use such as defined above, wherein the yeast cell walls have a dry matter content equal to or more than 90% preferably equal to or more than 94% and further preferably equal to or more than 96% by weight.

With said a dry matter content equal to or more than 90%, preferably equal to or more than 94%, and further preferably equal to more than 96%, it is possible to obtain better preservation of the yeast cell walls, notably better bacteriological stability and better stability against adverse reactions whether or not of enzymatic origin.

The subject of the present invention is the use of yeast cell walls such as defined above for the prevention and/or treatment of hyperinsulinaemia, whether basal or postprandial hyperinsulinaemia, irrespective of the origin of the hyperinsulinaemia.

The subject of the invention is particularly the use of yeast cell walls such as defined above for the prevention and/or treatment of hyperinsulinaemia associated with insulin-resistance, overweight, obesity or metabolic syndrome in any type of patient suffering from hyperinsulinaemia of this origin.

However, although the invention is intended for the prevention and treatment of any type of hyperinsulinaemia, in any type of patient, in one advantageous embodiment the yeast cell walls of the invention are used for the preparation of a medicinal product intended for the prevention and/or treatment of hyperinsulinaemia in a non-diabetic patient. In this case, the subject of the present invention is particularly the use of yeast cell walls such as defined above for the prevention and/or treatment of hyperinsulinaemia associated with insulin-resistance, with overweight, with obesity or metabolic syndrome in non-diabetic persons.

Alternatively, the yeast cell walls according to the invention can also be used for the preparation of a medicinal product intended for the prevention and/or treatment of hyperinsulinaemia in a patient with type-2 diabetes. The subject of the present is then notably the use of yeast cell walls such as defined above for the prevention and/or treatment of hyperinsulinaemia associated with insulin-resistance, overweight, obesity or metabolic syndrome in a person with type-2 diabetes.

By <<type-2 diabetes>> is also meant non-insulin-dependent diabetes NIDD. Type-2 diabetes is characterized by a fasting glycaemia of more than 1.26 g/L.

When fasting glycaemia is between 1.10 g/L and 1.26 g/L, the term glycaemia anomaly is used.

In particular, the subject of the present invention is the use of yeast cell walls such as defined above for the prevention and/or treatment of hyperinsulinaemia during the first stages of type-2 diabetes.

By <<insulin-resistance>> is meant the lack of response by insulin-dependent tissues to the action of insulin. The pancreas then continues to secrete insulin whose plasma level becomes too high.

By <<overweight>> or <<obesity>> is meant excess weight. In adults, overweight is characterized by a Body Mass Index (BMI) of between 25 and 30 kg/m$^2$ and obesity by a Body Mass Index (BMI) of more than 30 kg/m$^2$. The Body Mass Index in a person is defined by the following formula:

$$BMI = \frac{weight(kg)}{(height(m))^2}$$

The expression <<overweight or obesity in non-diabetic persons>> means overweight or obesity such as defined above in persons whose glycaemia is properly regulated.

In particular the glucose plasma level in fasting non-diabetic persons is less than 1.26 g/L (7 mmol/L) notably less than 1.10 g/L (6.1 mmol/L).

By the expression <<metabolic syndrome>> is meant a set of risk factors for developing cardiovascular disorders, strokes and type-2 diabetes.

The diagnosis of metabolic syndrome is based on the evaluation of several parameters, including waste size, cholesterol and triglyceride levels, fasting glycaemia, insulinaemia and blood pressure.

In particular, according to the NCEP-ATPIII (National Cholesterol Education Program—Adult Treatment Panel III), metabolic syndrome is diagnosed if three or more of the following risk factors are present:
- waist size of more than 88 cm in women and more than 102 cm in men
- HDL cholesterol level of less than 1 mmol/l in men and 1.2 mmol/l in women,
- triglyceride level equal to or more than 1.7 mmol/l
- fasting glycaemia equal to or more than 6.1 mmol/l
- blood pressure of over 130 mm Hg/85 mm Hg.

Postprandial hyperinsulinaemia may in particular play a role in the development of metabolic syndrome.

The present invention also concerns a method for the treatment and/or prevention of hyperinsulinaemia in a patient, comprising the administration to the patient of a pharmaceutical composition according to the invention.

The method for the treatment and/or prevention of hyperinsulinaemia can, in particular, be a method for the treatment and/or prevention of hyperinsulinaemia associated with insulin-resistance, overweight, obesity or metabolic syndrome. In one advantageous embodiment, the patient is a non-diabetic patient. Alternatively, the patient may also be a patient with type-2 diabetes.

The invention particularly concerns said method in which the pharmaceutical composition is administered to the patient via oral route.

The different methods according to the invention can in particular comprise administering to the patient the pharmaceutical composition in a daily dose corresponding to 1 to 10 g, preferably 8 to 9 g of yeast cell walls according to the invention, said daily dose possibly being administered in a single dose or at a single time of intake such as at breakfast, or in several partial doses i.e. spread out over the day.

The methods of the invention may also comprise at least one verification step to check the patient's basal insulin level and/or insulin response subsequent to food intake or to an OGTT test, after acute or chronic administration of the pharmaceutical composition.

The methods according to the invention can also comprise a measurement step to measure the patient's basal insulin level and/or to evaluate insulin response further to food intake or an OGTT test before acute or chronic administration of the above pharmaceutical composition.

The present invention also concerns a method to reduce or stabilize the basal plasma level of insulin in a patient suffering from basal hyperinsulinaemia, comprising the administration to the said patient of an effective quantity of a pharmaceutical composition according to the invention.

The method to reduce or stabilize the basal plasma level of insulin may particularly concern a patient suffering from basal hyperinsulinaemia associated with insulin-resistance, overweight, obesity, or metabolic syndrome. In one advantageous embodiment, the patient is a non-diabetic patient. Alternatively the patient may also be a patient with type-2 diabetes.

The present invention also concerns a method to reduce the insulin secretion peak after food intake in a patient suffering from postprandial hyperinsulinaemia comprising the administration to said patient of an effective quantity of a pharmaceutical composition according to the invention.

The method to reduce the insulin secretion peak further to food intake may in particular concern a patient having postprandial hyperinsulinaemia associated with insulin-resistance, overweight, obesity or metabolic syndrome. In one advantageous embodiment, the patient is a non-diabetic patient. Alternatively, the patient may also be a patient with type-2 diabetes.

The results of the 3 days of investigation are given as a mean±SEM. Insulinaemia in controls who had ingested milk is shown as a solid line with squares, in persons who had taken yeast cell walls devoid of mannans (beta-glucans) as a dashed line with diamonds, and in persons who had ingested yeast cell walls with mannans as a dotted line with triangles.

The insulin level (in mU/L) is given as a function of time in minutes (min).

Figure 2:
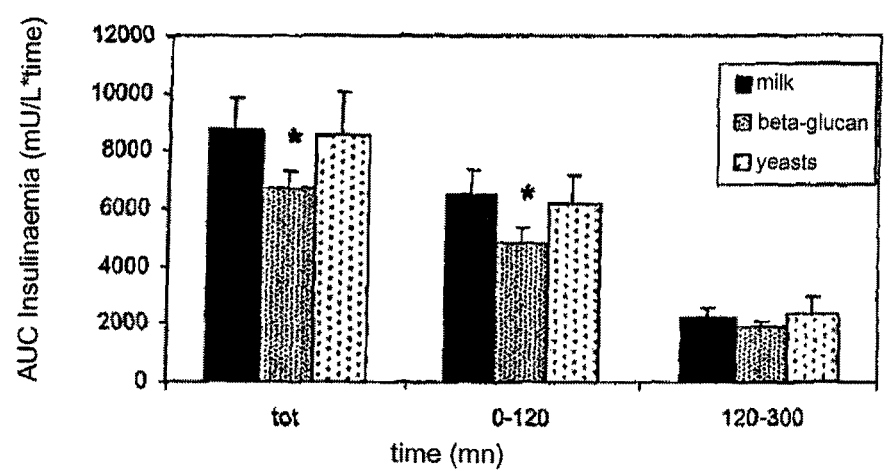

FIG. 2. Trend in postprandial insulinaemia shown as the area under curve (AUC) in overweight persons (n=12).

The results of 3 days' investigation are given as a mean±SEM. The area under curve obtained in control persons who had ingested milk is shown as a black line, in persons who had ingested yeast cell walls devoid of mannans (beta-glucans) as a close dotted line, and in persons who had ingested yeast cell walls with mannans in a spaced dotted line. The insulinaemia area (in mU/L*time) is given for the period 0-300 minutes (tot), the period 0-120 minutes and the period 120-300 minutes.

Figure 3:
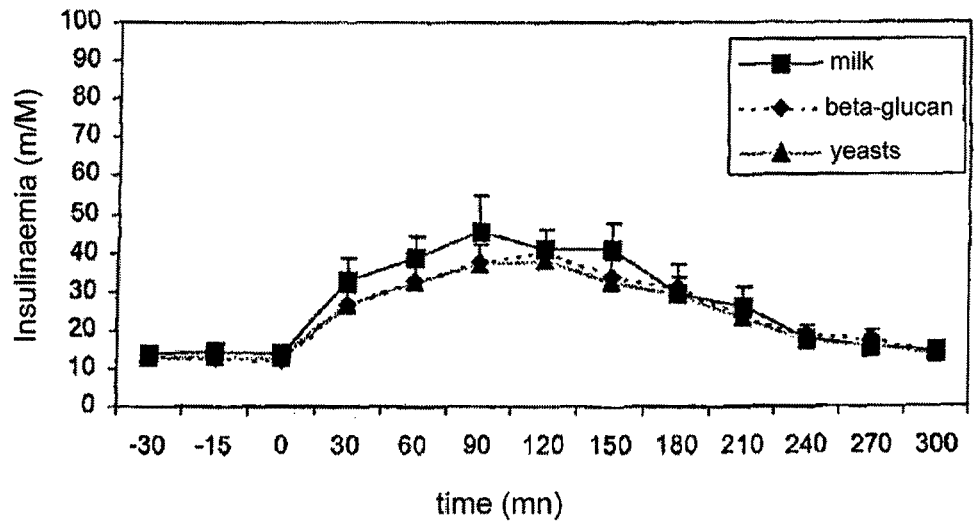

FIG. 3: Kinetics of postprandial insulinaemia in persons with type-2 diabetes (n=11).

The results of 3 days' investigation are given as a mean±SEM. Insulinaemia in controls who had ingested milk are shown as a solid line with squares, in those who had ingested yeast cell walls devoid of mannans (beta-glucans) as a dashed line with diamonds, and in persons who had ingested yeast cell walls with mannans as a dotted line with triangles. The insulin level (in mU/L) is given as a function of time in minutes (min).

Figure 4:
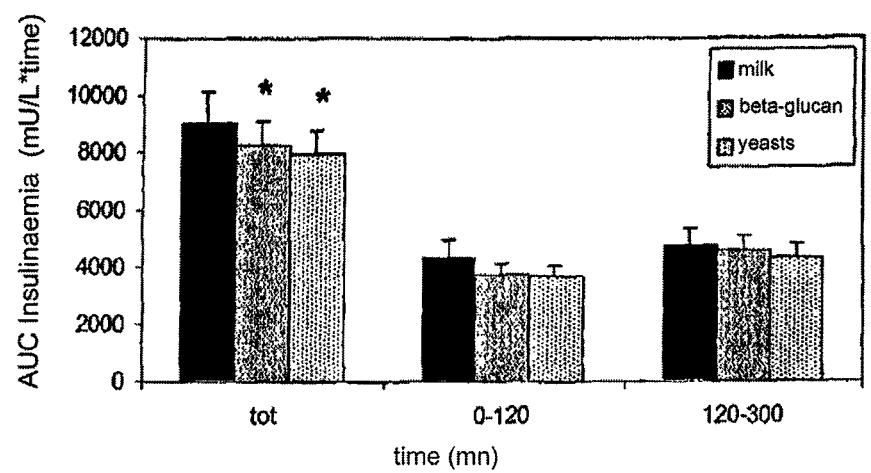

FIG. 4: Trend in postprandial insulinaemia shown as the area under curve (AUC) in patients with type-2 diabetes (n=11).

The results of the 3 days' investigation are given as a mean±SEM. The area of insulinaemia in controls who had ingested milk is given in black, in the persons who had ingested yeast cell walls devoid of mannans (beta-glucans) as a close dotted line, and in persons who had ingested yeast cell walls with mannans as a spaced apart dotted line. The insulinaemia area (in mU/L*time) is given for the period 0-300 minutes (tot), the period 0-120 minutes and the period 120-300 minutes.

EXAMPLES

Example 1

Preparation of Yeast Cell Walls According to the Invention

1. Material and Methods

Preparation of Yeast Cell Walls Containing Mannans

An aqueous cream (i.e. a suspension of yeast cells in water) of *Saccharomyces cerevisiae* having a dry matter content between 12 and 18% by weight is subjected to hydrolysis using endogenous enzymes of said yeast cells, optionally supplemented with proteases exogenous to the yeast cells, such as papain for example. Hydrolysis is conducted at 50° C. for 24 hours so as to solubilise at least 60% by weight of the dry matter of the yeast cells.

In practice and generally the autolyses and enzymatic hydrolyses of the invention are conducted at between 45° C. and 55° C. for 18 to 36 hours, without the use of any enzyme which may solubilise the glucans or mannoproteins.

The solubilised fraction is separated from the insoluble fraction in several successive steps by centrifuging and washing with water.

The insoluble fraction is dried on heated rolls to a dry matter content of 95% by weight. The agglomerates formed are removed by screening and the yeast cell walls of the invention are obtained.

Preparation of Yeast Cell Walls Devoid of Mannans

The yeast cell walls obtained previously are placed in an aqueous suspension and heated in an alkaline medium at between 70° C. and 100° C. for no more than three hours. In particular, the suspension in alkaline sodium hydroxide aqueous medium is heated to 85° C. for two hours.

The fraction solubilised by this treatment is removed, the remaining non-solubilised fraction being collected, washed and generally dried. The solubilised fraction containing the mannoproteins and also the glycogen is removed by centrifuging and washing.

The yeast cell walls obtained after the hot alkaline treatment are preferably subjected to an acid treatment to remove every trace of mannoprotein. The insoluble fraction is next acidified with phosphoric or acetic acid, then incubated at 80° C. for one to two hours. The solubilised fraction containing the residues of mannoproteins, glycogen and also some lipids is removed by centrifuging and washing.

Measurement of Glycogen Content

To a sample of 20 mg of dried yeast cell walls i.e. having a dry matter content of at least 90% by weight, is added 0.5 ml of 0.25 M $Na_2CO_3$ and this mixture is held at 95° C. for 4 hours.

The mixture is then brought to a pH of 5.2 by adding 0.3 ml of 1M acetic acid and 1.2 ml of 0.2M sodium acetate, and mixing the ingredients. Distilled water is added up to a total volume of 2 ml.

0.5 ml of the suspension thus obtained are incubated for 15 hours in the presence of excess amyloglucosidase of *Aspergillus niger*, such as marketed by ROCHE under Cat. No. 102 857, at 55° C.

After centrifuging, the released glucose is assayed by enzymatic assay.

The enzymatic assay of glucose is notably described in the manual <<Methods of Biochemical Analysis and Food Analysis—using Single reagents>>, published by BOEHRINGER MANNHEIM GmbH Biochemica© 1989, pages 50 to 55, and is preferably conducted using the "Test-Combination D-Glucose/-Fructose" Cat. No. 139 106 from the subsidiary of ROCHE: BOEHRINGER MANNHEIM GmbH/R-BIOPHARM GmbH Darmstadt Germany.

The quantity (in mg) of glucose thus assayed corresponds to the quantity of glycogen present in the sample expressed in glucose equivalent weight.

Measurement of the Total Content of Glucans and Mannans

A sample of 20 mg of dried yeast cell walls i.e. having a dry matter content of at least 90% by weight, is subjected to acid hydrolysis by mixing with 20 ml of 2N HCl, and the mixture is kept in a closed screw-top tube for 4 hours at 103° C. in an oven under agitation every 15 mn.

The acid solution thus obtained is then neutralized and the respective quantity of glucose and mannose is enzymatically assayed in the neutralized solution.

This enzymatic assay of glucose and mannose is also described on pages 50 to 55 of the above-cited manual and is preferably performed using the "Test-Combination" Cat. No. 139 106.

The difference is calculated between the quantity of glucose (expressed in mg) assayed using this method, and the quantity of glucose (also expressed in mg) assayed for these yeast cell walls using the above method to measure the glycogen content.

This difference (in mg) between the two assayed quantities of glucose corresponds to the total quantity of glucans present in the sample, this quantity being expressed in glucose equivalent weight.

The quantity (in mg) of assayed mannose corresponds to the total quantity of mannans present in the sample, this quantity being expressed in mannose equivalent weight.

2. Results

The yeast cell walls thus obtained have a dry matter content of 95% by weight.

The composition of yeast cell walls containing mannans and of yeast cell walls devoid of mannans (obtained by hot alkaline treatment) is given in Table 1.

TABLE 1

Composition of yeast cell walls according to the invention

|  | Yeast cell walls containing mannans | | Yeast cell walls devoid of mannans | |
| --- | --- | --- | --- | --- |
|  | Analysis in g per 100 g of product | Energy intake in Kcal/g | Analysis in g per 100 g of product | Energy intake in Kcal/g |
| Carbohydrates: | 49.9 | 2.046 | 55.1 | 2.259 |
| Glucans | 28.2 |  | 55.1 |  |
| Mannans | 21.7 |  | 0 |  |
| Proteins | 23.6 | 1.298 | 2.2 | 0.121 |
| Lipids | 11.8 | 1.109 | 21.6 | 2.03 |

For both types of yeast cell walls, the glycogen content was less than 10% dry matter content by weight.

Example 2

Effect of the Yeast Cell Walls of the Invention on the Insulin Level of Overweight Non-Diabetic Persons and of Non-Insulin-Dependent Diabetic Persons In the remainder, the yeast cell walls containing mannans are called <<yeast cell walls>> and the yeast cell walls devoid of mannans are called <<beta-glucans>>.

1. Material and Methods

Subjects, Characteristics and Sample Size 24 volunteers of 2 types were enrolled: 12 healthy overweight volunteers and 12 patients with type-2 diabetes (men or women).

For the overweight volunteers the inclusion criteria were: body mass index of between 25 and 30 $kg/m^2$ (limits included), age between 30 and 65 years (limits included), normal fasting glycaemia: <7 mmol/l, HbAlc: <6%, total cholesterol: ≤7.0 mmol/l, triglycerides: ≤4.0 mmol/l.

For the subjects with type-2 diabetes the inclusion criteria were: age of between 30 and 65 years (limits included), treatment with metformin and/or hypoglycaemic sulfamides and/or glinides and/or glitazones for at least 3 months, HbAlc: <10%, total cholesterol: ≤7.0 mmol/l, triglycerides: ≤4.0 mmol/l.

The main exclusion criteria were: type-1 diabetes, type-2 diabetes treated with insulin or acarbose, insulinopenia, chronic kidney or liver deficiency, case history of chronic gastro-intestinal disease, endocrine pathology, treatment possibly interfering with the metabolism of carbohydrates and eating behaviour, intolerance to cows' milk, claustrophobia (calorimetric measurements under Canopy®), pregnant women, persons consuming large quantities of products on the list of banned foods.

Only one diabetic person proved to be insulinopenic during the first induced hyperglycaemia and was therefore excluded from the trial since not complying with the defined inclusion criteria. The 23 other subjects completed the study.

Oral Glucose Tolerance Test (OGTT)

The trial took place over 3 days of hospitalisation separated by an interval of 7 to 14 days. Each subject was given each of the 3 OGTTs drawn in random order.

8 g of yeast cell walls and 9 g of beta-glucans were used in the OGTT tests. It is to be noted that the consumption of yeast cell walls at the planned dose of 8 g does not exceed the consumption levels observed for bakers' yeasts and food yeasts.

The products were diluted in 167 ml of a 30% $^{13}$Cglucose solution containing 50 g of $^{13}$Cglucose. For the placebo meal-test the 167 ml of $^{13}$Cglucose solution were supplemented with 28 ml of whole milk and 50 ml semi-skimmed milk to obtain an energy intake equivalent to 8 g of yeast cell walls and 9 g of beta-glucans.

The metabolic day was divided into two parts: a basal period (T-120 to T0) during which the basal conditions (fasting) were measured, then the postprandial period of 4h45 (T15-T300) consecutive to the OGTT test.

During the OGTT test the patient was given 50 g of $^{13}$Cglucose at T0. Depending on the random order, the possible extemporaneous addition was made to the solution either of yeast cell walls or of beta-glucans or milk. The solution was to be ingested in less than 10 minutes. The patient remained in decubitus position for the 5 following hours avoiding sleep. During the investigation day, the subject was allowed to drink water (300 ml maximum).

The plasma insulin levels were determined basally (between T-120 and T0) and in the postprandial period from T15 to T300. The venous samples were immediately centrifuged and the plasma collected for insulin assay. The assay of plasma insulin was performed by RadioImmuneassay (Medgenix Diagnostics®, Rungis France).

Statistical Treatment

The results are presented as a mean per group±the standard error of the mean (SEM). The results obtained with the 3 conditions (yeast cell walls, beta-glucans and placebo (milk)) were compared in pairs using the non-parametric Wilcoxon test on matched series. To perform these statistical tests the software used was Statview (Statview, Abacus Concepts, Berkeley, Calif.).

2. Results

Good digestive tolerance of both tested yeast products was observed.

Trend in Insulinaemia Throughout the 3 OGTT Tests in the Overweight Subjects

The increase in insulinaemia in response to the oral glucose intake was significantly lower in the presence of beta-glucans than with the placebo.

Figure 1:
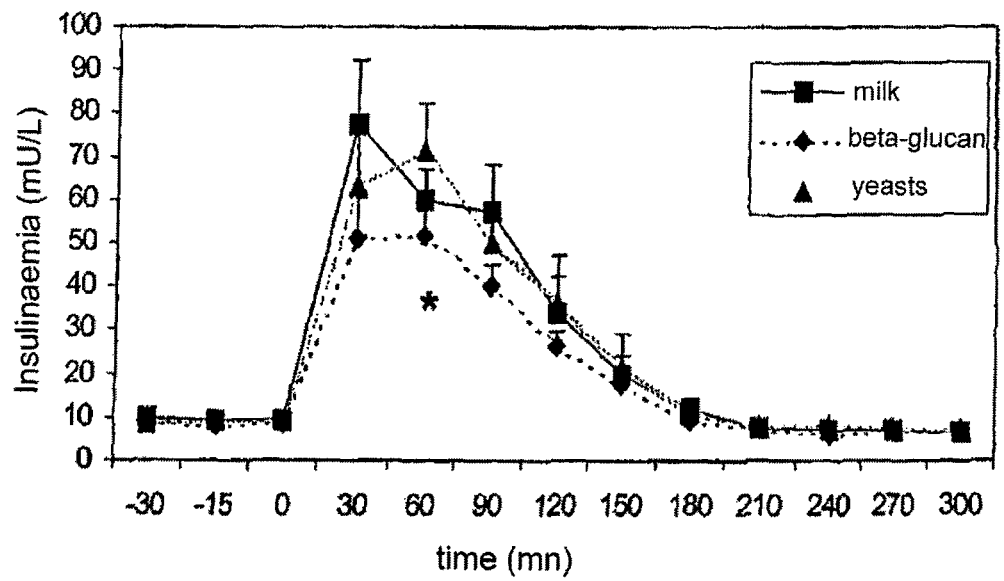
FIG. 1: Kinetics of postprandial insulinaemia in overweight patients (n=12).

The insulin peak was significantly lower in the presence of beta-glucans than with the placebo (63.0±7.7 mU/L versus 91.6±13.4 mU/L for the milk condition (p<0.01) (FIG. 1). The area under curve of insulinaemia in the presence of beta-glucans was significantly lower than with the placebo (p<0.05) (FIG. 2 and Table 2).

For the yeast cell walls, a trend towards a reduction in insulin peak and in the area under curve was observed compared with the placebo.

TABLE 2

Insulin peak in mU/L and insulinaemia areas under curve in mU/L*time in overweight subjects.

| Overweight insulinaemia | Milk | Yeast cell walls | Beta-glucans |
|---|---|---|---|
| Insulin peak | 91.6 ± 13.4 | 84.2 ± 13.2 | 63.0 ± 7.7 $p < 0.01$ |
| Area under curve 0-300 mn | 8715 ± 1130 | 8570 ± 1444 | 6736 ± 591 $p < 0.05$ |
| Area under curve 0-120 min | 6499 ± 903 | 6214 ± 960 | 4816 ± 504 $p < 0.05$ |
| Area under curve 120 min | 2216 ± 3 35 | 2356 ± 5 48 | 1920 ± 158 |

The results are expressed as a mean ± SEM (n = 12). $p < x$ = significant difference compared with placebo (milk).

Trend in Insulinaemia Throughout the 3 HGPO Tests in Type-2 Diabetes Subjects

In the type-2 diabetes subjects a reduction in insulin response was also observed in the presence of beta-glucans and in the presence of yeast cell walls.

The insulin peak was significantly reduced in the presence of both beta-glucans and yeast cell walls (respectively 44.2±6.0 mU/L and 43.8±4.7 mU/L versus 56.1±8.8 mU/L for milk, p<0.05) (FIG. 3 and Table 3).

The area under curve was significantly reduced in the presence of yeast cell walls and beta-glucans compared with the placebo (FIG. 4 and Table 3).

TABLE 3

Insulin peak in mU/L and insulinaemia area under curve in mU/l*time in type-2 diabetes subjects.

| Overweight insulinaemia | Milk | Yeast cell walls | Beta-glucans |
|---|---|---|---|
| Insulin peak | 56.1 ± 8.8 | 43.8 ± 4.7 $p < 0.05$ | 44.2 ± 6.0 $p < 0.05$ |
| Area under curve 0-300 min | 9049 ± 1070 | 7947 ± 821 $p = 0.05$ | 8248 ± 878 $p < 0.05$ |
| Area under curve 0-120 min | 4325 ± 619 | 3644 ± 381 | 3708 ± 404 |
| Area under curve 120 min | 4725 ± 587 | 430 ± 502 | 4540 ± 498 |

The results are expressed as a mean ± SEM (n = 11). $p < x$ = significant difference compared with placebo (milk).

The insulinaemia results in both populations, the non-diabetic overweight subjects and the type-2 diabetes subjects, therefore show a significant reduction in the insulin response after ingestion of yeast cell walls devoid of mannans. The same applies to the ingestion of yeast cell walls containing mannans in subjects with type-2 diabetes.

The invention claimed is:

1. A method of treatment of hyperinsulinemia in a patient in need thereof, comprising administering an effective amount of yeast cell walls to a non-hyperglycemic patient in need thereof, wherein said yeast cell walls have:
   a.) a total content of glucan and mannan of at least 34.0% dry matter content by weight; and
   b.) a glycogen content of less than 10.0% dry matter content by weight, wherein the non-hyperglycemic patient is overweight.

2. The method of claim 1, wherein the yeast cell walls obtained from *Saccharomyces cerevisiae*.

3. The method of claim 1, wherein said yeast cell walls have a total content of glucan and mannan of at least 40% dry matter content by weight.

4. The method of claim 1, wherein said yeast cell walls have a mannan content of less than 30% dry matter content by weight.

5. The method of claim 1, wherein said yeast cell walls have a mannan content of less than 2% dry matter content by weight.

6. The method of claim 1, wherein said yeast cell walls have a total content of glucan and mannan of 90% or less dry matter content by weight.

7. The method of claim 1, wherein said yeast cell walls have a total content of glucan and mannan of 45% to 90% dry matter content by weight.

8. The method of claim 1, wherein said yeast cell walls have a glycogen content of less than 8% dry matter content by weight.

9. The method of claim 1, wherein the yeast cell walls have a dry matter content of 90% or more dry matter content by weight.

10. The method of claim 1, wherein said yeast cell walls have a total content of glucan and mannan of at least 45% dry matter content by weight.

11. The method of claim 1, wherein said yeast cell walls have a mannan content less than 1% dry matter content by weight.

12. The method of claim 1, wherein the yeast cell walls have a total content of glucan and mannan equal to or less than 80% dry matter content by weight.

13. The method of claim 1, wherein the yeast cell walls have a total content of glucan and mannan of 52% to 80% dry matter content by weight.

14. The method of claim 1, wherein the yeast cell walls have a glycogen content of less than 5% dry matter content by weight.

15. The method of claim 1, wherein the yeast cell walls have a dry matter content of 94% or more.

16. The method of claim 1, wherein said yeast cell walls are obtained by:
   i.) submitting an aqueous suspension of yeast cells having a dry matter content between 12% and 18% by weight to hydrolysis using endogenous enzymes of said yeast cells and, optionally proteases exogenous to said yeast cells to provide an insoluble fraction;
   ii.) separating the insoluble fraction; and
   iii.) drying the separated insoluble fraction to obtain the said yeast cell walls, wherein the cells walls have a dry matter content of 90% by weight.

17. The method of claim 16, wherein hydrolysis is conducted at a temperature of between 45° C. and 55° C. for 18 to 36 hours so as to solubilise at least 60% by weight of the dry matter of said yeast cells.

18. The method of claim 16, wherein the drying step iii.) is performed by spray drying or drying on heated rolls.

19. The method of claim 16, wherein the method further comprising:
   iv.) heating the aqueous suspension of yeast cell walls of step i.) in an alkaline medium at a temperature of between 70° C. and 100° C. for no more than 3 hours; and
   v.) separating the insoluble fraction produced to obtain the yeast cell walls, wherein said yeast cell walls are β-glucan-enriched; and,
   and optionally:
   vi.) submitting the separated insoluble fraction of step ii.) to acid treatment; and
   vii.) collecting the insoluble fraction produced by acid treatment to obtain the yeast cell walls, wherein said yeast cell walls are β-glucan-enriched and devoid of mannans.

20. The method of claim 19, wherein the suspension of yeast cell walls is heated at 85° C. for 2 hours in an alkaline sodium hydroxide aqueous medium.

21. The method of claim 19, wherein the insoluble fraction produced by acid treatment is separated by centrifugation and washing, and optionally dried.

* * * * *